United States Patent [19]

Kaminsky, deceased et al.

[11] 3,959,480

[45] May 25, 1976

[54] POLYCYCLIC GAMMA-PYRONE-3-CARBOXALDEHYDE DERIVATIVES

[75] Inventors: Daniel Kaminsky, deceased, late of Parsippany, N.J., by Bernice R. Kaminsky, administratrix; Sylvester Klutchko, Hackettstown; Maximilian von Strandtmann, Rockaway, both of N.J.

[73] Assignee: Warner-Lambert Company, Morris Plains, N.J.

[22] Filed: Feb. 3, 1975

[21] Appl. No.: 546,587

Related U.S. Application Data

[60] Division of Ser. No. 480,647, June 19, 1974, Pat. No. 3,887,585, which is a continuation-in-part of Ser. No. 352,135, April 18, 1973, abandoned.

[52] U.S. Cl. .............................................. 424/283
[51] Int. Cl.² ........................................... A61K 31/35
[58] Field of Search .................................. 424/283

[56] References Cited

UNITED STATES PATENTS

| | | | |
|---|---|---|---|
| 3,859,442 | 1/1975 | Pfister et al. | 424/283 |
| 3,862,144 | 1/1975 | Kaminsky | 424/283 |
| 3,864,493 | 2/1975 | Cairns et al. | 424/283 |

*Primary Examiner*—Norman A. Drezin
*Attorney, Agent, or Firm*—Albert H. Graddis; Frank S. Chow; Anne M. Kelly

[57] ABSTRACT

Novel polycyclic gamma-pyrone derivatives having a carboxaldehyde group on the 3-position and optionally substituted on the 5, 6, 7, 8, 9 or 10 positions with a hydroxy, lower alkyl or lower alkoxy group are disclosed, as well as the corresponding N-substituted, formyl imine derivatives thereof. These compounds, and pharmaceutical compositions containing these compounds, are useful for the treatment of allergic conditions and for the treatment of hyperacidity.

2 Claims, No Drawings

POLYCYCLIC GAMMA-PYRONE-3-CARBOXALDEHYDE DERIVATIVES

CROSS REFERENCE TO RELATED APPLICATION

This application is a division of U.S. Ser. No. 480,647, filed June 19, 1974, now U.S. Pat. No. 3,887,585, which is a continuation-in-part of U.S. Ser. No. 352,135, filed Apr. 18, 1973, now abandoned.

SUMMARY OF THE INVENTION

This invention relates to novel polycyclic gamma-pyrone-3-carboxaldehyde derivatives having the formula I:

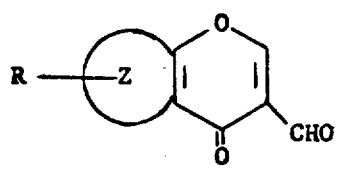

wherein R represents hydrogen, hydroxy, lower alkyl, or lower alkoxy and the Z ring has one of the following structures:

(a)
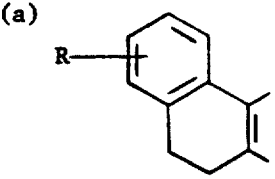

(b)
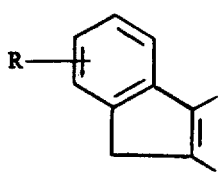

(c)
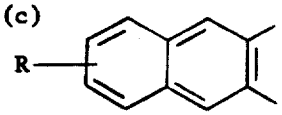

(d)
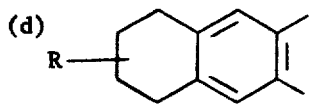

or (e)
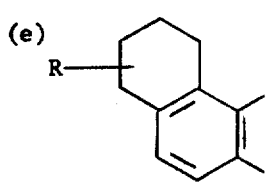

and the corresponding N-substituted, formyl imine derivatives thereof. These novel compounds, and novel pharmaceutical compositions containing these compounds, are useful for the treatment of allergic conditions and for the treatment of hyperacidity. In addition, compounds of the formula I wherein the Z ring represents:

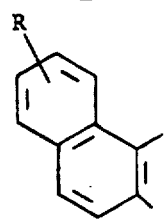

and R is as defined above, and pharmaceutical compositions containing these last-mentioned compounds, are useful for the treatment of allergic conditions and for the treatment of hyperacidity.

DETAILED DESCRIPTION OF THE INVENTION

The novel compounds of this invention have the general formula I:

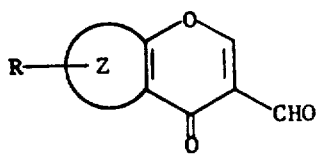

wherein R represents hydrogen, hydroxy, lower alkyl, or lower alkoxy and the Z ring has one of the following structures:

(a)
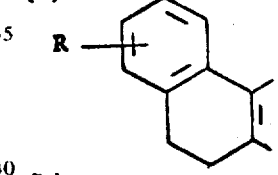

(b)
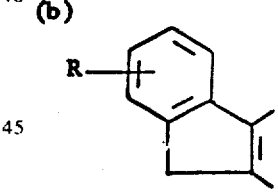

(c)
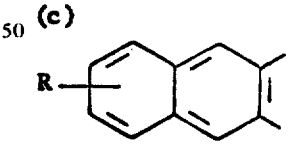

(d)

or (e)
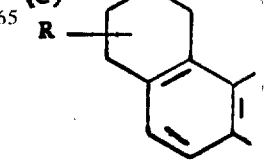

and the corresponding N-substituted, formyl imine derivatives thereof.

Derivatives of 3-formyl-gamma-pyrones, such as oximes, semi-carbazones, thiosemicarbazones, acetals and hydrazones, are also the subject of this invention.

As a particularly active class of compounds, there may be mentioned those compounds having formula I above, wherein the Z ring has the structure (a) and R represents hydrogen, hydroxy, methyl or methoxy, and the corresponding N-substituted, formyl imine derivatives thereof. Another particularly preferred class of compounds are those having formula I above, wherein the Z ring has the structure (b), (c), (d), or (e) and R represents hydrogen.

The novel compounds of this invention may be prepared by either of two different procedures. One process, described more fully in Ser. No. 351,912, filed Apr. 18, 1973, now U.S. Pat. No. 3,862,144, relates to the preparation of compounds of the general formula I wherein the Z ring has the structure (a) or (b); such compounds are represented in formula II:

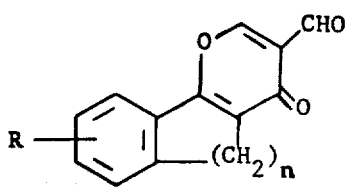

wherein R represents hydrogen, hydroxy, lower alkyl, or lower alkoxy, and $n$ represents 1 or 2. Compounds of the formula II are prepared by treating a compound of the formula III:

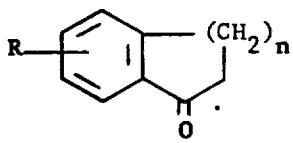

wherein R and $n$ are as described above, with an acetic anhydride and a boron trifluoride compound, preferably boron trifluoride etherate, to provide an intermediate of the formula IV:

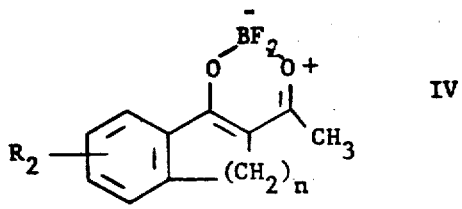

wherein R and $n$ are as described above and treating intermediate IV with a Vilsmeier reagent (phosphorus oxychloride and dimethylformamide), followed by hydrolysis.

The second process for preparing the novel compounds of this invention, is more fully described in U.S. Pat. No. 3,886,183 issued May 27, 1975. This second process relates to the preparation of compounds of the formula I wherein the Z ring has the structure (c), (d), and (e), that is, to compounds having the general formula V:

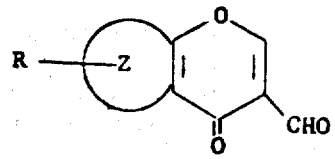

wherein R represents hydrogen, lower alkyl, or lower alkoxy and the Z ring has one of the following structures:

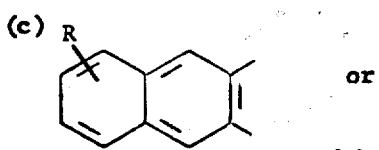

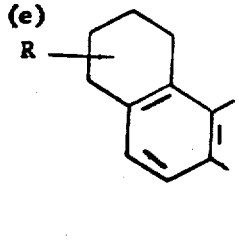

Compounds of the general formula V are prepared by oxidizing a compound of the formula VI:

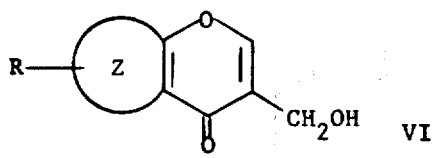

wherein R and the Z ring are as defined above, using an oxidizing agent selected from the group consisting of sodium dichromate-glacial acetic acid, concentrated nitric acid, and potassium persulfate. Starting materials VI and their precursors (as well as various derivatives thereof, containing one or more substituents on the naphtho ring) are described more fully in co-pending U.S. Ser. No. 112,765, filed Feb. 4, 1971, now abandoned; and in continuation-in-part (of said Ser. No. 112,765), application Ser. No. 309,329, filed Nov. 24, 1972, now U.S. Pat. No. 3,798,240; in continuation-in-part (of said Ser. No. 309,329), application Ser. No. 387,861 filed Aug. 13, 1973; and U.S. application Ser. No. 392,152, filed Aug. 27, 1973.

The above-mentioned compounds VI are prepared by reacting correspondingly substituted compounds having the formula VII:

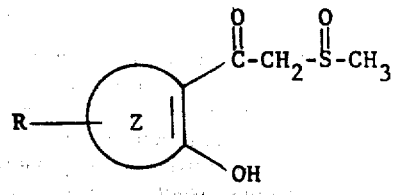

wherein R and Z are as defined above, with 2 moles of formaldehyde under basic conditions to obtain an intermediate compound having the formula VIII:

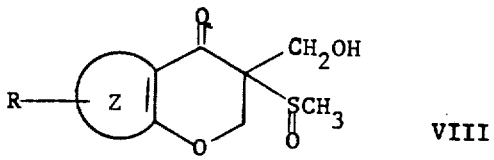

wherein R and Z are as defined above; and treating compound VIII thermally to eliminate methylsulfinic acid ($CH_3SOH$) and obtain the desired starting materials VI.

Compounds having the formula VII above are prepared by (A) reacting dimethyl sulfoxide with sodium hydride in an inert solvent; (B) adding to reaction mixture (A) an appropriately substituted ortho-hydroxynaphthoate (or tetrahydro derivative thereof); (C) maintaining the reaction mixture of (B) at a temperature of up to 50°C; (D) reducing the solubility of the sodium salt reaction product of (C) by the addition of a non-polar solvent; and (E) collecting the precipitate formed. A similar preparation has been reported by Becker et al., J.A.C.S. 85: 3410 (1963).

Substituted and unsubstituted 1-hydroxy-2-naphthoates (Ber. 20: 2700 (1887), substituted and unsubstituted 3-hydroxy-2-naphthoates (Ber. 25: 3635 (1892), and the corresponding 5,6,7,8-tetrahydro derivatives thereof (Ann. 426: 147, 158 (1922) are known or easily prepared by known methods.

Compounds of the general formula I wherein R represents hydrogen and the Z ring has the structure (f):

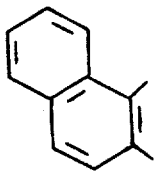

are disclosed in J. Het. Chem. 6: 375–377, June 1, 1969; no particular therapeutic activity for such compounds is reported in this reference. However, these compounds and their derivatives represented by the formula IX:

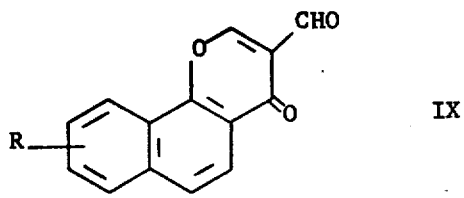

wherein R represents hydrogen, hydroxy, lower alkyl or lower alkoxy, have demonstrated, quite surprisingly, useful activity in the treatment of allergic conditions and in the treatment of hyperacidity.

Thus, the polycyclic gamma-pyrone-3-carboxaldehyde derivatives of this invention having formula I prepared by either of the two methods described above (and compounds of the general formula IX) have been found to reduce histaminic responses to antigen challenge by inhibiting antibody-antigen reactions in mammals such as rats or guinea pigs upon oral or parenteral administration. When tested in accordance with the procedure of Mota, Life Sciences, 7, 465, (1963) and Ovary, Proc. Soc. Exptl. Biol. Med., 81, 584, (1952) therapeutic compositions containing these compounds are effective at dosages of 5 mg to 50 mg/kg of body weight.

Pharmaceutical compositions containing the compounds of formula I are therefore useful in the management of allergic reactions such as bronchial asthma. To treat bronchial asthma, a dose of 5 mg to 50 mg/kg, administered orally or parenterally is suggested; in addition, aerosol administration of lower doses may be used. The dosage may be varied depending upon severity of the condition and the weight, age and sex of the patient being treated.

In use, the compounds of formula I and IX may be combined with a parenterally acceptable vehicle, such as a gum tragacanth saline suspension, to provide dosage forms suitable for parenteral administration; or they may be combined with pharmaceutical diluents such as lactose, cornstarch, and the like and formulated into tablet or capsule dosage forms. In order to enhance their therapeutic spectrum, the compounds of formula I may be combined with sympathomimetic agents such as isoprenaline or combined with steroids such as cortisone and its derivatives.

The compounds of formula I and IX also exhibit antisecretory effects and are therefore useful in relieving gastric hyperacidity. Gastric hyperacidity has generally been described as a factor which contributes to peptic ulcer. The compounds of formula I, when administered to mammals in a manner as described below, have been found to inhibit the gastric secretion of hydrochloric acid and are therefore effective in eliminating the resulting acidity in the stomach.

At a dosage of 20 mg/kg, administered intraperitoneally, the subject compositions are effective in reducing gastric acidity in the pylorus ligated rat when tested according to the procedure of H. Shay, Gastroenterology, 5, 43, (1945).

Pharmaceutical compositions containing the compounds of formula I are thus indicated in the management of gastric hyperacidity and the treatment of peptic ulcer resulting from such hyperacidity. For parenteral administration, the pharmaceutical compositions containing the compounds of formula I may be administered as aqueous suspensions for intramuscular injection. These are prepared, for example, by suspending the active ingredient in sterile water and packaging in ampules so as to provide a concentration of 1,000 mg of the active ingredient per dosage unit.

In all of the above represented formulas I through IX, definitions may be more fully described as follows: the term "lower alkyl" is meant to include lower aliphatic hydrocarbons having 1 to 4 carbon atoms in the carbon chain, such as methyl, ethyl, propyl, isopropyl, butyl, or isobutyl. This definition for lower alkyl also applies to the lower alkyl portion of "lower alkoxy".

To further illustrate the practice of this invention, the following examples are included:

EXAMPLE I

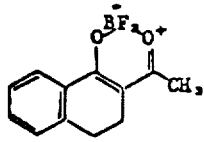

Preparation of
2,2-difluoro-5,6-dihydro-4-methylnaphtho[1,2-e]-1,3,2-dioxaborin - Method A Boron trifluoride etherate (100 g. – 0.7 mole) is added to a mixture of 73 g. (0.5 mole) α-tetralone in 204 g. (2.0 mole) of acetic anhydride. The mixture is heated on a steam bath for 2 hours (permitting volatiles to escape) and then gently refluxed for 1 hr. After standing overnight the mixture is triturated with cold ethyl acetate and filtered. The product is washed with ethyl ether and dried yielding 112 g. (95%) of greenish crystals; mp 156°–159°C. The analytical sample (from ethyl acetate) melted at 159°–160°C.

Anal. Calcd: $C_{12}H_{11}BF_2O_2$: C, 61.07; H, 4.70; F, 16.10. Found: C, 61.14; H, 4.72; F, 16.12.

EXAMPLE II

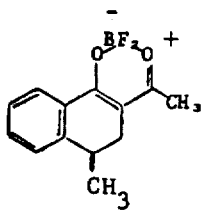

Preparation of
2,2-difluoro-5,6-dihydro-4,6-dimethylnaphtho-[1,2-e]1,3,2-dioxaborin Starting with 4-methyl-α-tetralone and using method A of Example I, 2,2-difluoro-5,6-dihydro-4,6-dimethylnaphtho[1,2-e]-1,3,2-dioxaborin is obtained having an mp of 120°–122°C.

Anal. Calcd: $C_{13}H_{13}BF_2O_2$: C, 62.44; H, 5.24; F, 15.20. Found: C, 62.47; H, 5.24; F, 15.21.

EXAMPLE III

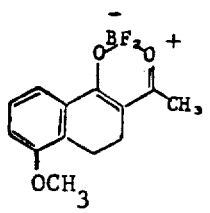

Preparation of
2,2-difluoro-5,6-dihydro-7-methoxy-4-methylnaphtho-[1,2-e]1,3,2-dioxaborin Starting with 5-methoxy-α-tetralone and using method A of Example I, 2,2-difluoro-5,6-dihydro-7-methoxy-4-methylnaphtho-[1,2-e]1,3,2-dioxaborin is obtained having an mp of 176°–177°C.

Anal. Calcd.: $C_{13}H_{13}BF_2O_3$: C, 58.69; H, 4.92; F, 14.28. Found: C, 58.62; H, 5.09; F, 14.24.

EXAMPLE IV

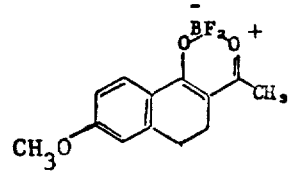

Preparation of
2,2-difluoro-5,6-dihydro-8-methoxy-4-methylnaphtho-[1,2-e]1,3,2-dioxaborin Starting with 6-methoxy-α-tetralone and using method A of Example I, 2,2-difluoro-5,6-dihydro-8-methoxy-4-methylnaphtho-[1,2-e]1,3,2-dioxaborin is obtained having an mp of 175°–176°C.

Anal. Calcd.: $C_{13}H_{13}BF_2O_3$: C, 58.69; H, 4.92; F, 14.28. Found: C, 58.36; H, 4.81; F, 14.23.

EXAMPLE V

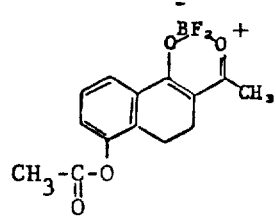

Preparation of
2,2-difluoro-5,6-dihydro-7-acetoxy-4-methylnaphtho-[1,2-e]1,3,2-dioxaborin Starting with 5-acetoxy-α-tetralone and using Method A of Example I, 2,2-difluoro-5,6-dihydro-7-acetoxy-4-methylnaphtho-[1,2-e]1,3,2-dioxaborin is obtained having an mp of 159°–160°C.

Anal. Calcd: $C_{14}H_{13}BF_2O_4$: C, 57.18, H, 4.46; F, 12.92. Found: C, 56.98; H, 4.41; F, 13.13.

EXAMPLE VI

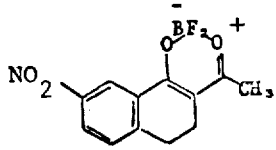

Preparation of
2,2-difluoro-5,6-dihydro-9-nitro-4-methylnaphtho-[1,2-e]1,3,2-dioxaborin Starting with 7-nitro-α-tetralone and using method A of Example I, 2,2-difluoro-5,6-dihydro-9-nitro-4-methylnaphtho-[1,2-e]1,3,2-dioxaborin is obtained having an mp of 176°–191°C.

Anal. Calcd: $C_{12}H_{10}BF_2NO_4$: C, 51.29; H, 3.59; F, 13.52. Found: C, 51.38; H, 3.53; F, 13.63.

EXAMPLE VII

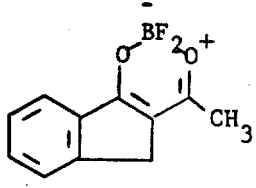

Preparation of
2,2-difluoro-4-methyl-5H-indeno[2,3-e]dioxaborin

Starting with indanone and using method A of Example I, 2,2-difluoro-4-methyl-5H-indeno[2,3-e]dioxaborin is obtained having an mp of 233°–235°C (dec.).

Anal. Calcd: $C_{11}H_9BF_2O_2$: C, 59.51; H, 4.09; F, 17.12. Found: C, 59.64; H, 4.12; F, 16.92.

EXAMPLE VIII

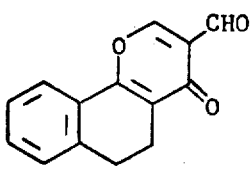

Method B - Preparation of
5,6-dihydro-4-oxo-4H-naphtho[1,2-b]pyran-3-carboxaldehyde Phosphorus oxychloride (153 g., 1.0 mole) is added dropwise to 365 g. (5.0 moles) of dimethyl formamide with cooling in order to maintain temperature below 10°C. The mixture is stirred for an additional 10–15 minutes and 118 g. (0.5 mole) of 2,2-difluoro-5,6-dihydro-4-methylnaphtho[1,2-e]1,3,2-dioxaborin is added. The mixture is then heated for 2 hours on a steam bath and poured cautiously into 4 liters of cold water. After standing for several hours with occasional stirring, the mixture is filtered to yield, after drying, 202 g. (89.5%) dark brown product; mp 153°–156°C. The analytical sample (from acetonitrile) melted at 154°–156°C.

Anal. Calcd for $C_{14}H_{10}O_3$: C, 74.33; H, 4.46; O, 21.22. Found: C, 74.33; H, 4.41; O, 21.05.

EXAMPLE IX

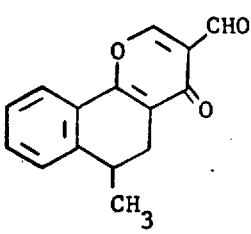

Preparation of
5,6-dihydro-6-methyl-4-oxo-4H-naphtho[1,2-b]pyran-3-carboxaldehyde Starting with 2,2-difluoro-5,6-dihydro-4,6-dimethylnaphtho-[1,2-e]1,3,2-dioxaborin and using method B of Example VIII, 5,6-dihydro-6-methyl-4-oxo-4H-naphtho[1,2-b]pyran-3-carboxaldehyde is obtained having an mp of 146°–148°C.

Anal. Calcd: $C_{15}H_{12}O_3$: C, 74.99; H, 5.03; O, 19.98. Found: C, 74.90; H, 5.07; O, 19.83.

EXAMPLE X

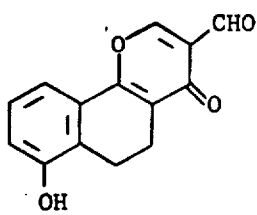

Preparation of
5,6-dihydro-7-hydroxy-4-oxo-4H-naphtho[1,2-b]pyran-3-carboxaldehyde Starting with 2,2-difluoro-5,6-dihydro-7-acetoxy-4-methylnaphtho[1,2-e]1,3,2-dioxaborin and using method B of Example VIII, 5,6-dihydro-7-hydroxy-4-oxo-4H-naphtho[1,2-b]pyran-3-carboxaldehyde is obtained having an mp of 255°–256°C. (dec.)

Anal. Calcd: $C_{14}H_{10}O_4$: C, 69.42; H, 4.16; O, 26.42. Found: C, 69.58; H, 5.20; O, 26.68.

EXAMPLE XI

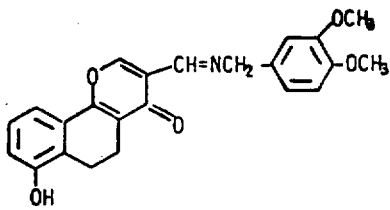

Preparation of
5,6-dihydro-7-hydroxy-3-(N-veratrylformimidoyl)-4H-naphtho[1,2-b]pyran-4-one monohydrate The product of Example X is reacted wth veratrylamine to obtain 5,6-dihydro-7-hydroxy-3-(N-veratrylformimidoyl)-4H-naphtho[1,2-b]pyran-4-one monohydrate having an mp of 157–159°C.

Anal. Calcd: $C_{23}H_{21}O_5N \cdot H_2O$: C, 67.46; H, 5.66; O, 23.45; N, 3.42. Found: C, 67.35; H, 5.75; O, 23.08; N, 3.48.

EXAMPLE XII

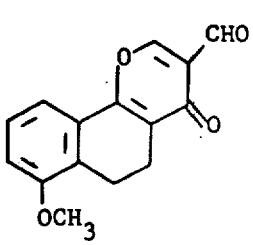

Preparation of
5,6-dihydro-7-methoxy-4-oxo-4H-naphtho[1,2-b]-
pyran-3-carboxaldehyde Starting with 2,2-difluoro-5,6-dihydro-7-methoxy-4-methylnaphtho[1,2-e]1,3,2-dioxaborin and using method B of Example VIII, 5,6-dihydro-7-methoxy-4-oxo-4H-naphtho[1,2-b]-pyran-3-carboxaldehyde is obtained having an mp of 201°–202°C.

Anal. Calcd: $C_{15}H_{12}O_4$: C, 70.30; H, 4.72. Found: C, 70.23; H, 4.73.

EXAMPLE XIII

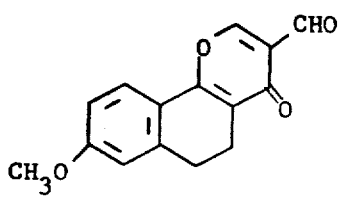

Preparation of
5,6-dihydro-8-methoxy-4-oxo-4H-naphtho[1,2-b]pyran-3-carboxaldehyde Starting with 2,2-difluoro-5,6-dihydro-8-methoxy-4-methylnaphtho[1,2-e]1,3,2-dioxaborin and using method B of Example VIII, 5,6-dihydro-8-methoxy-4-oxo-4H-naphtho[1,2-b]pyran-3-carboxaldehyde is obtained having an mp of 186°–187°C. (dec.)

Anal. Calcd: $C_{15}H_{12}O_4$: C, 70.30; H, 4.72; O, 24.98. Found: C, 70.11; H, 4.77; O, 24.78.

EXAMPLE XIV

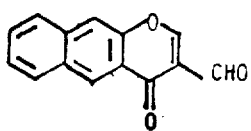

Method C: Preparation of
4-Oxo-4H-naphtho[2,3-b]pyran-3-carboxaldehyde

A slurry of 1.6 g (0.007 mole) of 3-(hydroxymethyl)-4H-naphtho[2,3-b]pyran-4-one in 10 ml of glacial acetic acid is added to a stirred solution of 2.11 g (0.007 mole) of sodium dichromate dihydrate, keeping the temperature at 40°C. with mild cooling. After the initial exotherm, the reaction is stirred at room temperature overnight. Water (100 ml) is added and the resulting turbid solution is heated to 75°C. to generate a precipitate. The cooled mixture is filtered and the crude product (1.4 g) is purified by filtration of a methylene chloride solution through a layer of silica gel, wt. 0.22 g (14%), mp 215–218°C. Recrystallization from ethylacetate gives pure aldehyde; mp 220°–222°C.

Anal. Calcd: $C_{14}H_8O_3$: C, 75.00; H, 3.60. Found: C, 74.88; H, 3.67.

EXAMPLE XV

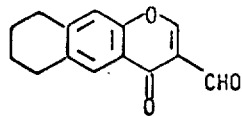

Method C: Preparation of
3-Formyl-6,7,8,9-tetrahydro-4H-naphtho-[2,3-b]pyran-4-one A mixture of 2.3 g (0.01 mole) of 3-(hydroxymethyl)-6,7,8,9-tetrahydro-4H-naphtho[2,3-b]pyran-4-one and 15 ml of glacial acetic acid is added to a solution of 2.98 g (0.01 mole) of sodium dichromate dihydrate in 15 ml of glacial acetic acid, keeping the temperature at about 50°C. with mild cooling. After 15 minutes, the reaction is heated at 60°C. for 15 minutes, water (100 ml) is added and the mixture is heated at 50°C. for 5 minutes. The separated solid is filtered, washed with water and dried; wt. 1.6 g (70%); mp 120°–123°C. Purification is effected by dissolving in methylene chloride and filtering through a layer of silica gel. The pure aldehyde is obtained by removal of solvent from the filtrate; mp 128°–130°C.

Anal. Calcd: $C_{14}H_{12}O_3$: C, 73.67; H, 5.30. Found: C, 73.54; H, 5.20.

EXAMPLE XVI

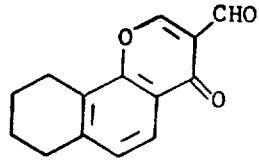

Method C: Preparation of
3-Formyl-7,8,9,10-tetrahydro-4H-naphtho[1,2-b]pyran-4-one This compound is prepared by adding a mixture of 23.0 g (0.1 mole) of 3-(hydroxymethyl)-7,8,9,10-tetrahydro-4H-naphtho-[1,2-b]pyran-4-one and 150 ml of glacial acetic acid to a solution of 29.8 g (0.1 mole) of sodium dichromate dihydrate in 150 ml of glacial acetic acid, keeping the temperature at about 50°C with cooling. After the initial exotherm, the reaction is heated at 60°C for one-half hour, water (1-liter) is added, and the mixture is heated at 75°C for about one-half hour to generate a precipitate. The cooled mixture is filtered and the crude product is purified by dissolving in methylene chloride and filtering through a layer of silica gel. The aldehyde is obtained by removal of solvent from the filtrate.

EXAMPLE XVII

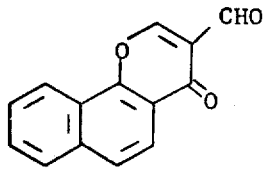

Method C: Preparation of
3-Formyl-4H-naphtho[1,2-b]pyran-4-one

A solution 8.44 g (0.028 mole) of sodium dichromate dihydrate in 30 ml of glacial acetic acid is added to a stirred mixture of 6.4 g (0.028 mole) of 3-(hydroxymethyl)-4H-naphtho[1,2-b]-pyran-4-one and 40 ml glacial acetic acid. The reaction is exothermic. The temperature is prevented from going over 50°C with cooling. After one-half hour at 35°–50°C the solution is heated to 70°C for one-half hour, water (200 ml) is added. The mixture is cooled and the separated crude solid is collected. Purification is effected by filtration of a methylene chloride solution through a layer of silica gel. In this fashion 1.0 g (16%) of pure aldehyde is obtained, mp 178°–180°C.

Anal. Calcd: $C_{14}H_8O_3$: C, 74.99; H, 3.60. Found: C, 75.08; H, 3.74.

We claim:

1. A method for preventing asthmatic symptoms in a mammal in need thereof which comprises the administration of an effective amount of a compound of the formula I:

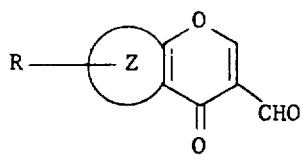

wherein R represents hydrogen, hydroxy, lower alkyl, or lower alkoxy and the Z ring has one of the following structures:

(a) 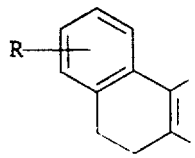

(b) 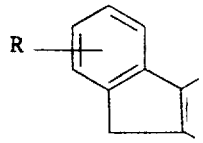

(c) 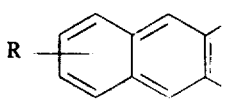

(d) 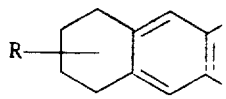

(e) 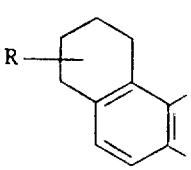

or (f) 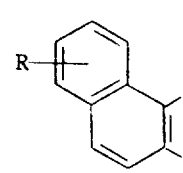

2. A method according to claim 1 wherein from 5 to 50 mg/kg of a compound having the formula I is administered.

* * * * *